United States Patent [19]

Weaver

[11] 4,085,756
[45] Apr. 25, 1978

[54] METHOD AND APPARATUS FOR PERFORMING AN ELECTROSURGICAL PROCEDURE

[76] Inventor: Kenneth Weaver, 1511 N. Main St., Waynesville, N.C. 28786

[21] Appl. No.: 728,122

[22] Filed: Sep. 30, 1976

Related U.S. Application Data

[63] Continuation-in-part of Ser. No. 594,203, Jul. 9, 1975, Pat. No. 4,000,743.

[51] Int. Cl.$^2$ ............................................. A61B 17/36
[52] U.S. Cl. .................................. 128/303.17; 128/17; 128/303.14
[58] Field of Search ..................... 128/17, 239, 303 R, 128/303.14, 303.15, 303.16, 303.17, 347

[56] References Cited

U.S. PATENT DOCUMENTS

| | | | |
|---|---|---|---|
| 1,620,828 | 3/1927 | Molony | 128/303.17 |
| 1,620,929 | 3/1927 | Wallerich | 128/303.17 X |
| 1,731,069 | 10/1929 | Herman | 128/303.16 |
| 1,770,653 | 7/1930 | Molony | 128/303.17 |
| 1,919,543 | 7/1933 | Doane | 128/303.17 X |
| 2,858,826 | 11/1958 | Kahn | 128/17 |
| 3,763,860 | 10/1973 | Clarke | 128/347 X |
| 3,877,433 | 4/1975 | Librach | 128/303 R |
| 3,938,527 | 2/1976 | Rioux et al. | 128/303.17 |
| 4,005,714 | 2/1977 | Hiltebrandt | 128/303.17 |

*Primary Examiner*—Robert W. Michell
*Assistant Examiner*—Michael H. Thaler
*Attorney, Agent, or Firm*—Bell, Seltzer, Park & Gibson

[57] ABSTRACT

A method and apparatus for performing an electrosurgical operative procedure which is particularly useful in sterilizing a human female by cutting and coagulating the fallopian tubes. The procedure includes inserting an active terminal of an electrosurgical apparatus through the abdominal wall, and inserting the ground terminal through the vagina and into the uterine cavity. Thus when the surgical current is applied to the fallopian tubes, the current travels a very short distance through the body to the ground terminal to thereby reduce the possibility of burns or other injury which is often associated with the use of conventional ground plates which contact the exterior surface of the patient's body. Also, the ground terminal may include means for manipulating the uterus into an anterior position to facilitate the visualization of the uterus and fallopian tubes by the surgeon through a laparoscope.

12 Claims, 8 Drawing Figures

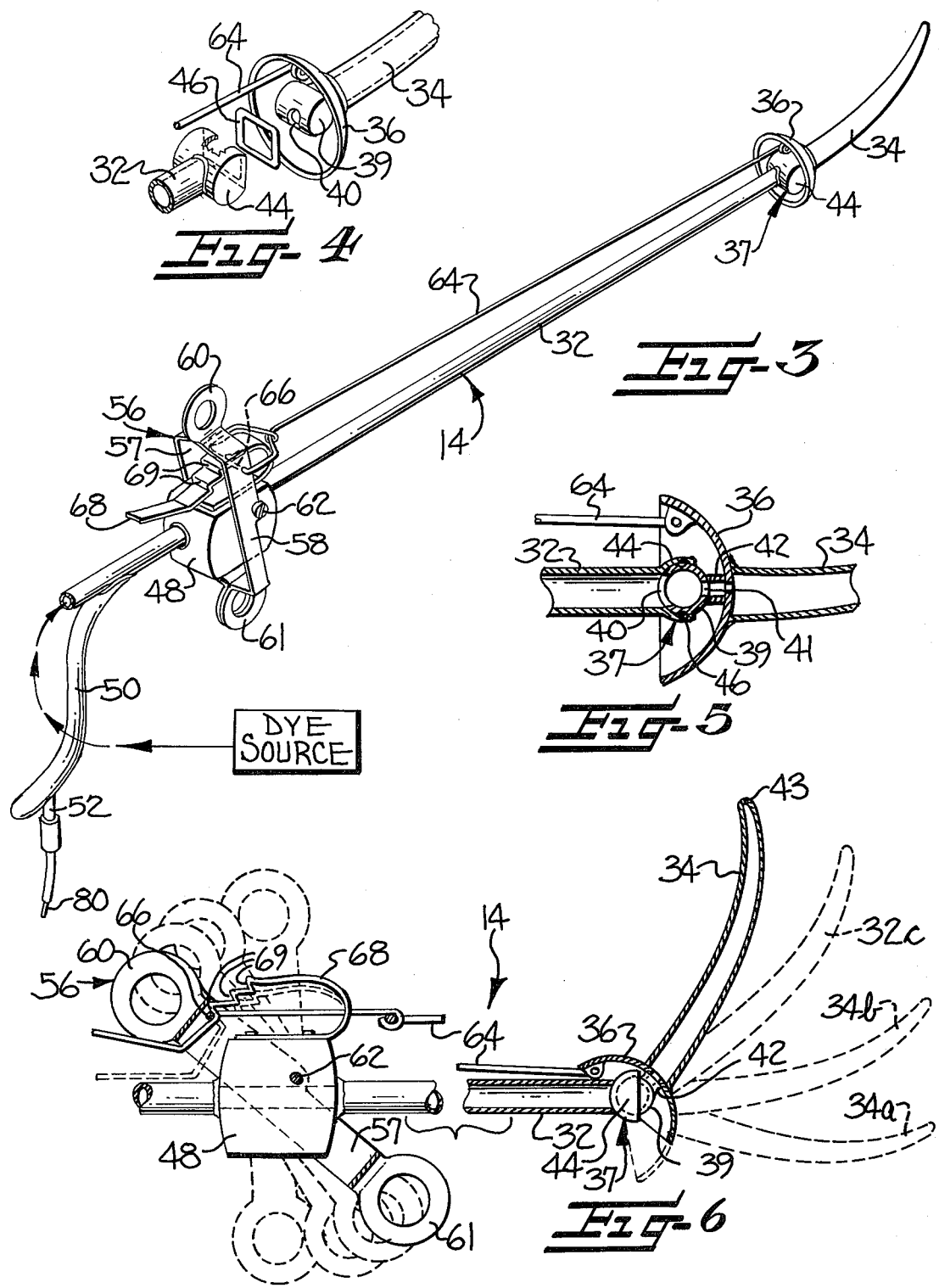

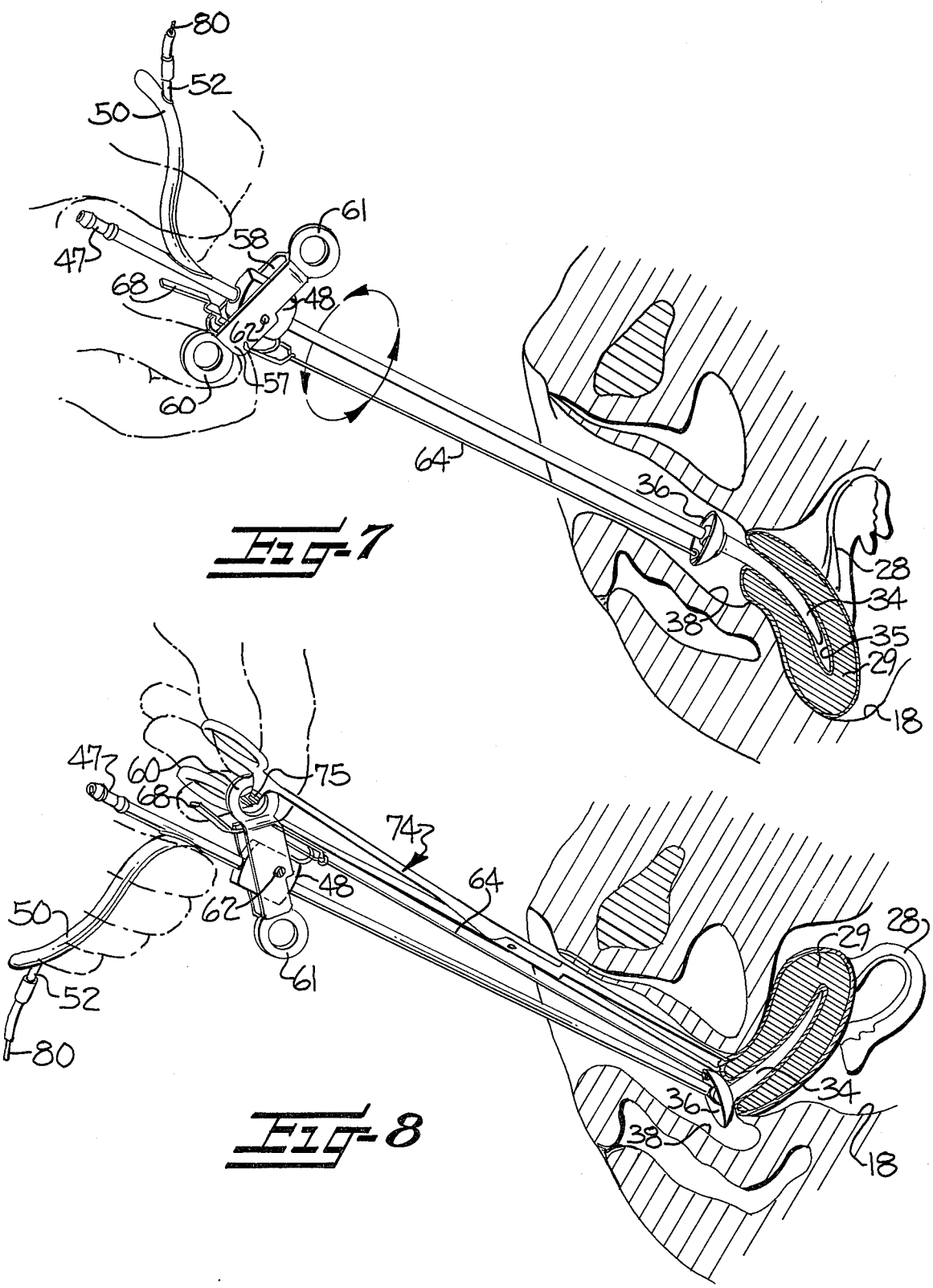

METHOD AND APPARATUS FOR PERFORMING AN ELECTROSURGICAL PROCEDURE

The present invention is a continuation-in-part of application Ser. No. 594,203 filed July 9, 1975, now U.S. Pat. No. 4,000,743.

The present invention relates to an electrosurgical operative procedure, and which is characterized by the absence of the conventionally employed external ground plate, and by the ability to manipulate the uterus into an anterior position to facilitate the visualization of the peritoneal cavity by the surgeon.

Conventional electrosurgery involves the use of an active electrode or terminal in the form of a needle, bulb, or forceps, and which receives a high frequency electrical current from a generator to cut and/or coagulate body tissue. A ground plate is positioned to contact the external surface of the body of the patient to collect the current and return the same to the generator and thereby complete the circuit.

One common electrosurgical procedure involves the coagulation of the fallopian tubes for sterilizing the human female. In this procedure, a small incision is made in the wall of the lower abdomen and a laparoscope is inserted therethrough to permit visualization of the peritoneal cavity by the surgeon. The active terminal of the electrosurgical apparatus is also inserted into the abdomen, and it is brought into contact with the fallopian tubes to effectively cut and coagulate the same, with the current being collected by a plate positioned beneath the body of the patient.

A common problem associated with the above described electrosurgical procedure resides in the fact that the ground plate often does not achieve proper electrical contact with the body, and electrical burns on the adjacent skin often result. Also, it is possible that accidental burns may occur on internal tissue, such as the bowel, from stray electrical current as it passes through the body.

In an attempt to avoid the above problems, bipolar coagulating instruments have recently been developed wherein both the active and ground terminals are positioned closely adjacent to each other on the surgical instrument which is inserted into the peritoneal cavity. Such devices have not proven to be satisfactory however, since the close proximity of the two electrodes limits the power which may be supplied to the instrument, and the use of low power often results in incomplete cutting of the tissue and the physical attachment of the active terminal of the instrument to the tissue. Further, such bipolar devices are not compatible with conventional generators in view of their different power requirements, thereby requiring the owners of present equipment to purchase a new and expensive generator in order to convert to the bipolar system.

A further problem associated with the above described tubal coagulation procedure resides in the fact that the uterus of many women, and particularly women who have borne children, is in an abnormal or retroverted position and extends downwardly into the peritoneal cavity. When so located, it is extremely difficult for the surgeon to visualize the uterus and fallopian tubes, and the danger of an improper or incomplete procedure, such as incomplete coagulation of the tubes, or contact of the instrument with the bowel or adjacent tissue, is increased.

It is accordingly an object of the present invention to provide an electrosurgical method and apparatus which avoids the above noted problems of the prior art systems.

It is a more particular object of the present invention to provide an electrosurgical method and apparatus which does not employ an external ground plate, and which thereby avoids the associated problem of external burns on the body of the patient.

It is another object of the present invention to provide an electrosurgical method and apparatus wherein the ground terminal is brought into close proximity with the active terminal by inserting the ground terminal into a natural body orifice, and which may be operated at a sufficiently high power setting to achieve proper cutting and coagulation of the tissue.

It is still another object of the present invention to provide an electrosurgical method and apparatus wherein the ground terminal is in the form of a manipulating instrument which is adapted to position a retroverted uterus into an anterior position to thereby facilitate the visualization thereof during the procedure. Further, once the instrument has manipulated the uterus into the desired anterior position, the instrument is able to hold and maintain the uterus in such position without further attention from the physician during the remainder of the procedure.

These and other objects and advantages of the present invention are achieved in the embodiment illustrated herein by a method and apparatus for performing an electrosurgical procedure which includes the steps of applying an electrosurgical current to tissue within a cavity of the body, and grounding the current through a terminal positioned within a natural body orifice and in close proximity of the tissue being acted upon. In a preferred embodiment, the current is grounded by means of a ground terminal which is positioned within the uterine cavity. Also, the ground terminal is preferably in the form of a uterus manipulating instrument having a pivotal arm carried at the forward end of an elongate rod, and such that the pivotal arm may be inserted into the uterine cavity and then pivoted to an upright position to thereby move the uterus into an anterior position and thereby facilitate visualization of the uterus and fallopian tubes through a laparoscope.

Some of the objects of the invention having been stated, other objects will appear as the description proceeds, when taken in connection with the accompanying drawings, in which FIG. 1 is a diagrammatic view of an apparatus embodying the features of the present invention and illustrating the same in an operative position within the peritoneal cavity of a patient;

FIG. 3 is a perspective view of the ground terminal as shown in FIG. 1 and which also serves as a uterine manipulating instrument;

FIG. 4 is a fragmentary exploded perspective view of the pivotal interconnection between the rod and forward arm of the instrument shown in FIG. 3;

FIG. 5 is a fragmentary sectional view of the pivotal interconnection between the rod and forward arm;

FIG. 6 is a side elevation view of the instrument, partly sectioned, and illustrating the manner in which the forward arm may be pivoted by the physician;

FIG. 7 is a diagrammatic view of the manipulating instrument in position within the vagina and uterus, with the uterus being shown in an abnormal or retroverted position; and FIG. 8 is a diagrammatic view similar to FIG. 7, and illustrating the uterus after having been manipulated to its normal or anterior position.

Figure 1:
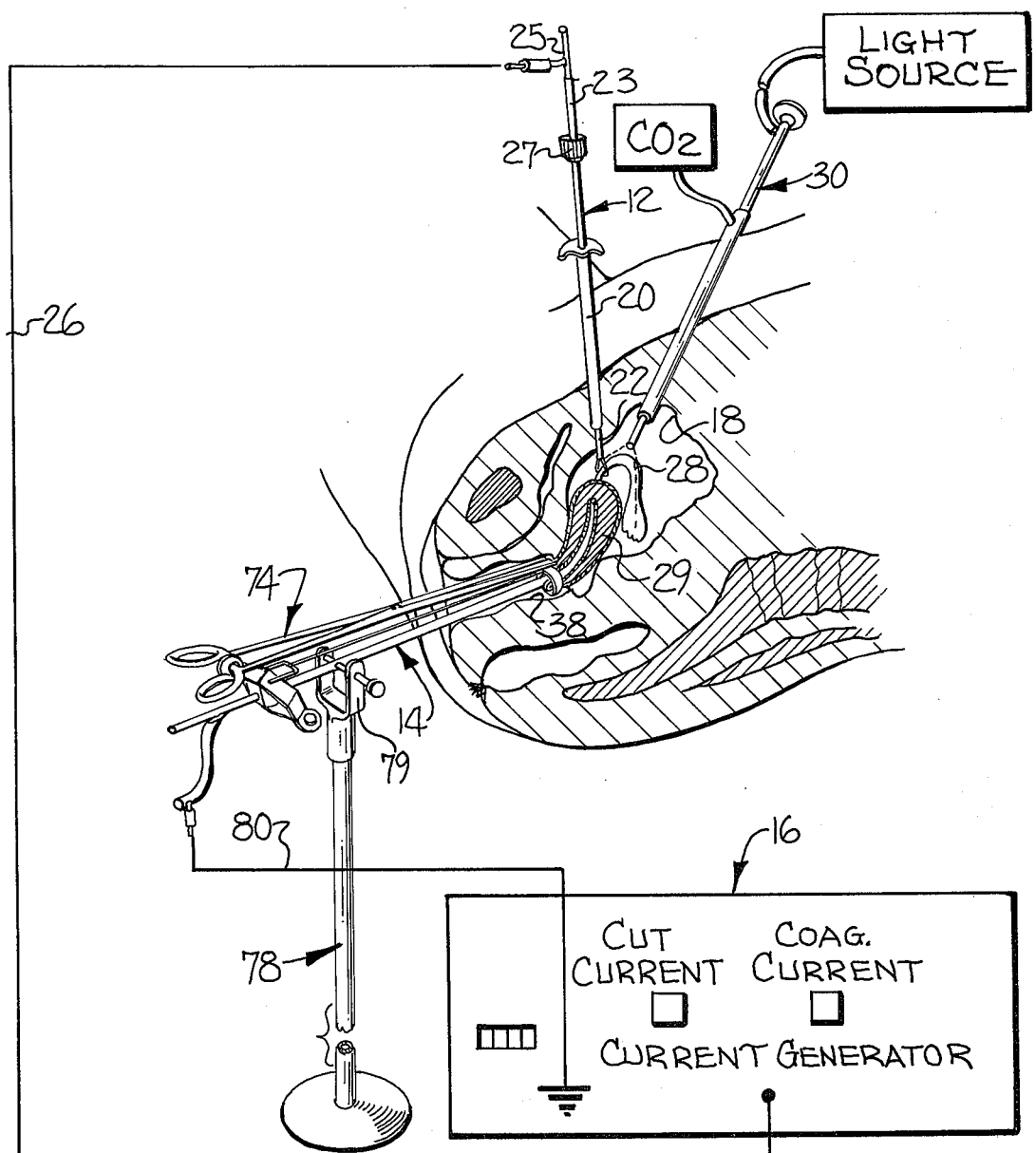
Figure 2:
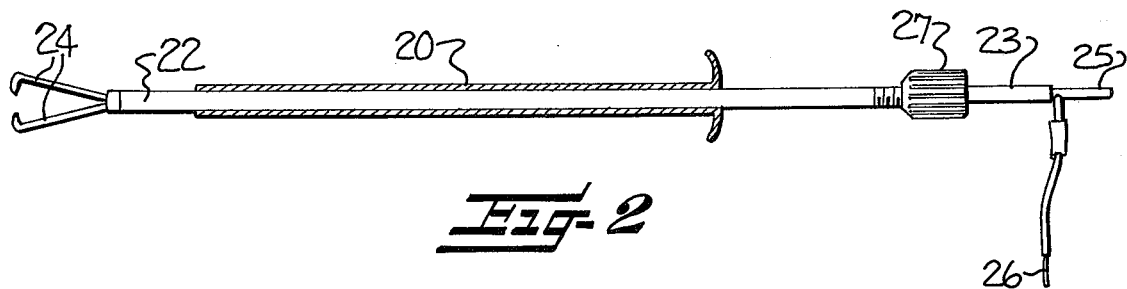
FIG. 2 is an elevation view of the active electrode or terminal as shown in FIG. 1.

Referring more particularly to FIG. 1 in the drawings, there is illustrated an electrosurgical apparatus in accordance with the present invention and which is useful, for example, in sterilizing a human female by cutting and coagulating the fallopian tubes. The apparatus generally comprises an active electrode or terminal 12, a ground electrode or terminal 14, and a high frequency current generator 16 operatively connected to each of the active and ground terminals.

The active terminal 12 is conventional, and in its operative position as shown in FIG. 1, it extends into the peritoneal cavity 18 of the patient through a trocar sleeve 20 which has been inserted through a small incision in the lower abdomen. The terminal 12 may take a variety of structural forms depending upon the specific tissue being acted upon, and in the illustrated embodiment, the terminal comprises an insulator 22 having a rod 23 slidably disposed therein, and with a pair of forceps 24 at the lower end of the rod such that relative sliding movement between the rod and sleeve causes the foreceps to open and close. The rod 23 and thus the forceps 24 are operatively connected to the generator 16 by means of a post 25 which is adapted to mate with a connector on the wire 26. Also, the rod 23 rotatably carries a nut 27 which threadedly engages the insulator 22, such that rotation of the nut causes the rod to slide within the insulator and the forceps 24 to grasp the desired tissue, which in the illustrated embodiment comprises one of the fallopian tubes 28 which are attached to the uterus 29. To permit the visualization of the peritoneal cavity 18 by the surgeon during the procedure, a laporoscope 30 of a type well known in the art is also inserted through the abdominal wall in the manner shown in FIG. 1. As illustrated schematically in FIG. 1, the laparoscope 30 includes a light source, and means for introducing carbon dioxide into the abdomen to extend the wall in the conventional manner.

The generator 16 of the apparatus 10 is also conventional, and is adapted to produce a high frequency electrosurgical current to cut and/or coagulate tissue. Typically, the generator 16 is adapted to selectively produce an undamped current which serves to cut the tissue, a highly damped current for coagulation, and a blended current which results in both cutting and coagulation.

In accordance with the present invention, the ground terminal 14 is in the form of a uterus manipulating instrument, such that the instrument serves to both manipulate the uterus 29 into a desired anterior position and also ground the electrosurgical current from a point closely adjacent the active terminal 12. Structurally, the instrument (or ground terminal) 14 comprises an elongate rod 32 having a length of between about seven to eight inches, and a forward manipulating arm 34 pivotally mounted at the forward end of the rod. The arm 34 has a length sufficient to extend a substantial distance into the uterine cavity 35 as seen in FIGS. 7 and 8, and it is arcuately curved along its length to approximate the natural curvature of the uterine cavity. In this regard, the rear end portion of the arm coaxially carries an arcuately curved shield 36 positioned immediately adjacent the pivotal connection at 37 with the rod. By this arrangement, the distance which the arm 34 may be inserted into the uterine cavity 35 is limited. Also, the shield 36 serves to effectively preclude contact between the pivotal connection 37 and wall 38 of the vagina of the patient during use and which could otherwise produce lacerations and trauma on the wall 38 during manipulation of the forward arm 34.

The rod 32 and arm 34 are preferably both fabricated from a tubular electrically conductive metallic material and the means for pivotally attaching the arm to the rod includes a passageway extending therebetween. More particularly, the pivotal interconnection includes a hollow cylindrical member 39 fixedly mounted to the rear end of the arm 34, the member 39 extending generally transversely to the axis of the arm. The cylindrical member 39 has closed opposite ends, and further includes a pair of aligned apertures 40 and 41 which communicate through the tubular attaching member 42 to the interior or bore of the arm 34. Also, the forward end of the arm includes an exit opening 43 for the purposes set forth below.

The forward end of the rod 32 includes a mating receptacle 44 which is adapted to substantially receive the cylindrical member 39 of the arm so as to permit relative pivotal movement about a transverse pivotal axis and in a vertical plane as seen in FIGS. 3 and 6. The receptacle 44 communicates with the bore of the tubular rod 32, such that in its assembled configuration, the bore of the rod 32 communicates with the bore of the tubular arm, note FIG. 5. This assembled configuration may be maintained by crimping the edges of the receptacle 44 about the cylindrical member 38, and also, a pivot pin (not shown) may be positioned to extend along the pivotal axis and through the receptacle 44 and cylindrical member 38 to more positively interconnect the two members. In addition, this interconnection between the rod and arm serves to establish and maintain an electrical interconnection therebetween for the reasons to become apparent. A sealing ring 46 may also be interposed between the receptacle and cylindrical member to sealably interconnect the two members.

The rear end of the rod 32 mounts a nipple, such as a conventional Luer connector 47 for the purposes set forth below, and a mounting block 48 is fixedly mounted to the rod immediately adjacent the rearward end thereof. Also, a curved handle 50 extends rearwardly and downwardly from the rear end of the rod to facilitate manual gripping thereof by the physician, note FIGS. 7 and 8. The handle 50 may be fabricated from a tubular material similar to that of the rod 32, but the bore thereof preferably does not communicate with the bore of the rod. Also, the handle 50 carries an electrical terminal or post 52 for the purposes set forth below.

The forward manipulating arm 34 is pivotally controlled by an arrangement which includes a cross bar 56 carried by the mounting block 48 of the rod. More particularly, the cross bar 56 includes parallel side legs 57, 58 which straddle the block 48 and which extend laterally in opposite directions from the rod 32 in a generally vertical plane as seen in FIG. 1. The upper ends of the legs 57, 58 are directed inwardly and are joined to define a first open ring 60 positioned above the mounting block 48, and the lower ends of the legs are similarly joined to define a second open ring 61 below the mounting block. The cross bar 56 is pivotally secured to the mounting block by means of a cross pin 62 which extends through the legs and mounting block to define a horizontal pivotal axis. Further, a rigid wire 64 is provided which has one end pivotally attached to the shield 36 and the other end pivotally attached to the upper portion of the legs 57, 58 such that the arm 34 may be selectively pivoted between a first position substantially coaxial with the rod, and a second generally upright position as seen in solid lines in FIG. 6. More particularly, the arm 34 is pivoted between a first coaxial position 34a as seen in FIG. 6, a pair of intermediate positions 34b and 34c and a fully upright position as seen in solid lines.

To releasably hold the arm 34 in one of its intermediate, or its fully upright position, there is provided a locking arrangement which includes a transverse segment 66 of the wire which extends between the legs 57, 58 of the cross bar, and a spring biased catch 68 carried by the upper surface of the mounting block. The catch comprises a flexible spring steel member or the like, and includes a number of locking shoulders 69. The wire segment 66 thus acts as a latching member which is adapted to lock behind one of the shoulders 69 when the cross bar 56 and arm 34 are pivoted into one of the intermediate or fully upright positions. To release the inter-engagement, the physician merely presses downwardly on the catch 68 to separate the locking shoulders 69 from the wire segment 66, and permit the cross bar to pivot rearwardly.

The manner in which the instrument 14 is utilized to manipulate the uterus 29 may be best described with reference to FIGS. 7 and 8. In this regard, it will be understood that the instrument 14 is commonly used in association with a conventional speculum, which has not been shown in the drawings for clarity of illustration.

Initially, the orientation of the uterus 29 is determined by the physician by a pelvic examination. As seen in FIG. 7, the uterus 29 is shown in the retroverted position, in which event the instrument 14 is inverted so that the manipulating arm 34 may be inserted into the uterine cavity 35 with the curvature of the arm 34 substantially following the natural curvature of the cavity 35. In this regard, it will be noted that the shield 36 serves to limit the extent to which the arm 14 may be inserted into the cavity, and further serves to protect the cervix and wall 38 of the vagina from contact with the pivotal interconnection 37 between the rod 32 and arm 34.

After insertion, the instrument 14 is rotated by the physician to lift the uterus slightly, and the forward arm 34 is then pivoted by pulling the upper portion of the cross bar 66 rearwardly. The latching member 66 freely slides downwardly over the shoulders 69 of the catch 68, and is automatically engaged by the most rearward shoulder. The uterus is thereby lifted to the desired anterior position as shown in FIG. 8 to lift and expose the fallopian tubes 28, and the arm 34 is automatically locked in its upright position by the catch 68.

To retain the apparatus and uterus in the desired position as seen in FIG. 8, a conventional tenaculum 74 is positioned to grip the anterior lip of the cervix, with the latching or toothed portion 75 of the tenaculum extending through the open ring 60. In this regard, tenacula of this type come in a variety of sizes and lengths, and one is chosen which will properly mate with the apparatus so that the latching portion 75 may be received through the open ring 60. Thus the ring 60 serves to releasably attach the instrument 14 to the tenaculum, and thereby assures that the instrument may be retained in its operative position within the uterine cavity 35. More particularly, the tenaculum 74 is attached to the anterior lip of the cervix, and the instrument 14 is attached to the tenaculum 74, thereby precluding withdrawal of the apparatus from the uterine cavity. Since pivotal movement of the forward arm 34 is also precluded by the catch 68, the proper positioning of the uterus 29 is assured during the remaining portion of the operative procedure.

In order to further assure retention of the instrument 14 and uterus in the desired position, a second tenaculum (not shown) may be attached to the posterior lip of the cervix, with the latching portion thereof extending through the lower open ring 61. In this case, two tenacula would concurrently engage the cervix, with each being releasably secured to the instrument 14. Here again, the size of the second tenaculum will be chosen so as to properly mate with the lower open ring 61.

The instrument 14 is preferably fabricated entirely from suitable metallic materials, such as stainless steel, to permit the entire instrument to be easily sterilized by autoclaving.

A floor stand 78 may also be provided for use in association with the present invention, and which includes a clamp 79 for further supporting the instrument 14 once it is operatively positioned and retained within the uterine cavity 35. Since the electrosurgical current will pass through the instrument 14, the stand 78 should be electrically insulated from the instrument, such as by forming the clamp 79 from a non-conductive material.

Where it is desired to perform a sterilization procedure in accordance with the present invention, the instrument 14 is inserted through the vagina and into the uterine cavity 35 in the manner described above. The uterus is then manipulated into the desired anterior position, and is held in such position by the catch 68. The active terminal 12 of the apparatus and the laparoscope 30 are then inserted through the wall of the abdomen as shown in FIG. 1, and the active terminal 12 and instrument 14 are operatively connected to the generator 16. In this regard, the wire 80 which extends between the instrument 14 and generator 16 may be releasably attached to the post 52 on the handle of the instrument 14.

A surgical cutting and coagulating current is then applied to each of the fallopian tubes by contacting the same with the active terminal 12, with the current being collected by the manipulating arm 34 of the instrument 14 which is positioned within the uterus 29. The current passes from the arm 34 along the rod 32, and is carried to the generator 16 via the wire 80. By this arrangement, the current passes only a relatively short distance through the body of the patient, to thereby minimize the opportunity for burns or other injury.

While the instrument (or ground terminal) 14 of the present invention is described herein for use as part of an electrosurgical apparatus 10, it will be understood that the instrument 14 may be independently used in other unrelated operative procedures. For example, certain operative procedures involve the injection of a dye into the uterine cavity. The instrument 14 of the present invention is adapted to perform this function, with the dye entering through the entry port at the connector 47, passing through the rod 32, and exiting through the exit port 43 at the remote free end of the arm 34.

In the drawings and specification, there has been set forth a preferred embodiment of the invention, and although specific terms are employed, they are used in a generic and descriptive sense only and not for purposes of limitation.

That which is claimed is:

1. A method of performing electrosurgery within a body cavity and characterized by the absence of a ground plate in contact with the exterior body surface of the patient and comprising the steps of
applying an electrosurgical current to tissue within the lower peritoneal cavity of the body, and while
grounding the current through a terminal positioned within and contacting the uterine cavity so as to be located in the proximity of the tissue to which the current is applied and such that the current travels a relatively short distance through the body.

2. The method as defined in claim 1 wherein the step of applying an electrosurgical current includes applying the current to the fallopian tubes.

3. A method of sterilizing a human female by electrosurgically cutting and coagulating the fallopian tubes, and comprising the steps of
inserting an electrically conductive elongate member into the uterine cavity and so as to contact the same,
inserting the active terminal of an electrosurgical instrument through the abdominal wall and into the lower peritoneal cavity,
applying a surgical current to each of the fallopian tubes by contacting the same with the active terminal to thereby cut and coagulate the tubes, and
grounding the surgical current through the member positioned within the uterine cavity.

4. The method as defined in claim 3 wherein the step of inserting the elongate member into the uterine cavity includes manipulating the uterus into an anterior position by manipulating the member into a predetermined orientation, and maintaining such predetermined orientation of the member during the remainder of the sterilizing procedure.

5. The method as defined in claim 4 comprising the further step of inserting a laparoscope through the abdominal wall to permit the visualization of the lower peritoneal cavity by the surgeon during the step of applying a current to the fallopian tubes.

6. In an electrosurgical apparatus useful, for example, in sterilizing a human female by cutting and coagulating the fallopian tubes, and having an active terminal, a ground terminal, and a high frequency current generator operatively connected to each of the active and ground terminals, the improvement wherein said ground terminal comprises
an elongate rod having a forward end portion adapted to be inserted through the vagina and into an operative position in the uterine cavity, and a rearward end portion adapted to remain outside the body when the forward end portion is in said operative position, and with at least said forward end portion being fabricated of an electrically conductive material, whereby the electrosurgical current employed in the procedure is collected by said forward end portion and thus passes a relatively short distance through the body of the patient to minimize the opportunity for burns or other injury.

7. The apparatus as defined in claim 6 wherein said rear end portion is fabricated from an electrically conductive material which serves to convey an electric current from said forward end portion along said rear end portion to facilitate the electrical interconnection of said ground terminal with said current generator.

8. In an electrosurgical apparatus useful, for example, in sterilizing a human female by cutting and coagulating the fallopian tubes, and having an active terminal, a ground terminal, and a high frequency current generator operatively connected to each of the active and ground terminals, the improvement wherein said ground terminal comprises
an elongate rod having a forward end adapted to extend into the vagina, and a rearward end,
a manipulating arm of an electrically conductive material pivotally mounted at said forward end of said rod, said arm having a configuration and length which permits the same to extend a substantial distance into the uterine cavity,
means carried at said rearward end of said rod and operatively connected to said arm for selectively pivoting said arm between a first position substantially coaxial with said rod and a second generally upright position which is angularly disposed with respect to said rod, and
means for releasably holding said arm in said upright position,
whereby a retroverted uterus may be moved to and maintained in an anterior position by inserting said arm into the uterine cavity and pivoting the same to its upright position to thereby facilitate visualization of the uterus and fallopian tubes through a laparoscope or the like, and wherein the electrosurgical current employed in the procedure is collected by said manipulating arm and thus passes a relatively short distance through the body of the patient to minimize the opportunity for burns or other injury.

9. The apparatus as defined in claim 8 wherein said ground terminal further comprises means for releasably attaching the same to a tenaculum such that said arm of said ground terminal may be retained within the uterine cavity by attaching the tenaculum to the anterior or posterior lip of the uterus and attaching the ground terminal to the tenaculum.

10. The apparatus as defined in claim 9 wherein said ground terminal further comprises a shield coaxially disposed about said arm immediately adjacent the pivotal connection to said rod to limit the distance which said arm may be inserted into the uterine cavity and to effectively preclude contact between the pivotal connection and the body of the patient during the use.

11. The apparatus as defined in claim 10 wherein said rod and arm are each fabricated from an electrically conductive metallic material whereby the electrosurgical current collected by said manipulating arm is conveyed to said rearward end of said rod to facilitate the electrical interconnection of said ground terminal with said current generator.

12. An apparatus for moving a retroverted uterus to an anterior position to facilitate visualization of the uterus during a laparoscopic procedure or the like, and characterized by the ability to serve as the ground terminal during an electrosurgical procedure in the lower peritoneal cavity, and comprising
an elongate rod having a forward end adapted to extend into the vagina, and a rearward end,
a manipulating arm of an electrically conductive material pivotally mounted at said forward end of said rod, said arm having a configuration and length which permits the same to extend a substantial distance into the uterine cavity,
means carried at said rearward end of said rod and operatively connected to said arm for selectively pivoting said arm between a first position substantially coaxial with said rod and a second generally upright position which is angularly disposed with respect to said rod, means for releasably holding said arm in said upright position, and an electrical terminal mounted adjacent the rearward end of said rod and electrically connected to said manipulating arm, whereby a retroverted uterus may be moved to and maintained in an anterior position by inserting said arm into the uterine cavity and pivoting the same to its upright position to thereby facilitate visualization of the uterus and fallopian tubes through a laparoscope or the like, and wherein the current employed in an electrosurgical procedure within the lower peritoneal cavity may be collected by said manipulating arm and grounded through said electrical terminal.

* * * * *